United States Patent
Moeller et al.

[11] Patent Number: 5,743,919
[45] Date of Patent: Apr. 28, 1998

[54] ISATIN DERIVATIVES FOR COLORING KERATIN-CONTAINING FIBERS

[75] Inventors: Hinrich Moeller, Monheim; Horst Hoeffkes, Duesseldorf, both of Germany

[73] Assignee: Henkel Kommanditgesellschaft auf Aktien, Duesseldorf, Germany

[21] Appl. No.: 716,207

[22] PCT Filed: Mar. 8, 1995

[86] PCT No.: PCT/EP95/00848

§ 371 Date: Sep. 17, 1996

§ 102(e) Date: Sep. 17, 1996

[87] PCT Pub. No.: WO95/24886

PCT Pub. Date: Sep. 21, 1995

[30] Foreign Application Priority Data

Mar. 17, 1994 [DE] Germany ............ 44 09 143.5

[51] Int. Cl.$^6$ ............................................. A61K 7/13
[52] U.S. Cl. ............... 8/409; 8/407; 8/423; 8/405; 8/563; 8/574
[58] Field of Search ................... 8/407, 409, 423, 8/563, 602, 574, 649, 405; 548/485

[56] References Cited

U.S. PATENT DOCUMENTS

| | | | |
|---|---|---|---|
| 4,212,804 | 7/1980 | Coppola | 548/485 |
| 4,750,908 | 6/1988 | Rosenbaum et al. | 8/429 |
| 5,190,564 | 3/1993 | Lang et al. | 8/423 |
| 5,261,926 | 11/1993 | Lang et al. | 8/406 |
| 5,340,366 | 8/1994 | Lang et al. | 8/406 |

FOREIGN PATENT DOCUMENTS

| | | |
|---|---|---|
| 35 94 65 | 3/1990 | European Pat. Off. |
| 497 697 | 8/1992 | European Pat. Off. |
| 502 783 | 9/1992 | European Pat. Off. |
| 502 784 | 9/1992 | European Pat. Off. |
| 36 35 147 | 4/1987 | Germany . |
| 93/19725 | 10/1993 | WIPO . |

*Primary Examiner*—Douglas J. McGinty
*Assistant Examiner*—Caroline L. Dvsheck
*Attorney, Agent, or Firm*—Ernest G. Szoke; Wayne C. Jaeschke; Real J. Grandmaison

[57] ABSTRACT

The process of coloring keratin-containing fibers by contacting the fibers with an isatin derivative corresponding to formula (I):

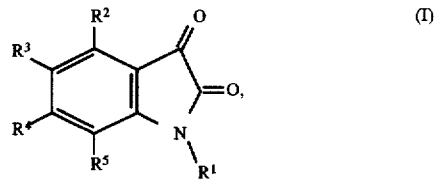

in which $R^1$ is a hydroxy group, an optionally $C_{1-4}$-alkyl- or phenyl-substituted amino group, a $C_{3-8}$ alkenyl, dihydroxy-$(C_{3-6})$-alkyl, trihydroxy-$(C_{4-6})$-alkyl, tetrahydroxy-$(C_{5-6})$-alkyl, pentahydroxy-$C_6$-alkyl, $C_{2-4}$-aminoalkyl, $C_{1-4}$-sulfoalkyl group, an optionally $C_{1-4}$-alkyl-substituted 2-furylmethyl, 2-thienylmethyl, 2-pyridylmethyl, 3-pyridylmethyl, 4-pyridylmethyl group or an aralkyl group corresponding to formula (II):

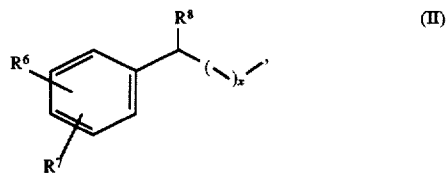

in which $R^6$ and $R^7$ independently of one another represent hydrogen, halogen atoms, hydroxy groups, amino groups optionally substituted by $C_{1-4}$ alkyl or phenyl, $C_{1-4}$ alkyl groups, $C_{1-4}$ alkoxy groups, carboxy groups or sulfo groups and $R^8$ is hydrogen, a $C_{1-4}$ alkyl group or a $C_{2-4}$ hydroxyalkyl group and x=0, 1 or 2, and $R^2$, $R^3$, $R^4$ and $R^5$ independently of one another represent hydrogen, hydroxy groups, halogen atoms, nitro groups, sulfo groups, carboxyl groups, $C_{1-4}$ alkyl groups, $C_{1-4}$ alkoxy groups or $NR^9R^{10}$ groups, wherein $R^9$ and $R^{10}$ independently of one another represent hydrogen, $C_{1-4}$ alkyl groups or $C_{2-4}$ hydroxyalkyl groups, and two adjacent groups $R^3$, $R^4$ and $R^5$ may represent an alkylenedioxy group containing 1 to 4 carbon atoms, and water-soluble salts thereof.

26 Claims, No Drawings

ISATIN DERIVATIVES FOR COLORING KERATIN-CONTAINING FIBERS

BACKGROUND OF THE INVENTION

1. Field of the Invention

This invention relates to the use of certain N-substituted isatin derivatives for coloring keratin-containing fibers and to coloring formulations containing these isatin derivatives.

Keratin-containing fibers, for example hair, wool or furs, are generally colored either with substantive dyes or with oxidation dyes which are formed by oxidative coupling of one or more primary intermediates with one another or with one or more secondary intermediates. Although intensive colors with good fastness properties can be obtained with oxidation dyes, development of the color takes place under the effect of oxidizing agents, such as $H_2O_2$ for example, which frequently results in damage to the fibers. Although substantive dyes are applied under more moderate conditions, their disadvantage is that the colors often have unsatisfactory fastness properties.

2. Discussion of Related Art

Coloring systems based on isatin or isatin derivatives offer an alternative solution. Isatin is described in DE-OS 36 35 147 A1 as a substantive dye for coloring keratin fibers either on its own or in conjunction with quinone dyes. Unfortunately, the range of variation of the color tones obtainable is limited. In most cases, a golden color is obtained.

Another isatin-containing coloring system is described in EP 359 465 A2. In this case, the color is obtained with a ketimine (Schiff's base) produced by the reaction of an isatin with an aniline derivative. The ketimine is either applied as such to keratin fibers where it develops color or, alternatively, a mixture consisting of an isatin and an aniline derivative is applied to the fibers and initially forms the ketimine in situ, after which the color develops on the fibers.

EP 497 697 A1 describes hair coloring formulations based on isatins and aminoindoles or indolines containing a primary amino group, Schiff's bases being formed in a condensation reaction.

EP 0 502 783 A1 describes hair coloring formulations containing isatins and aminopyridines or isatins and aminopyrimidines containing a primary amino group.

EP 0 502 784 A1 describes hair coloring formulations containing isatins and substituted diamines or aminophenols or isatins and (bisaryl) alkylenediamines.

Unfortunately, the hair colors obtainable with these isatins are not always satisfactory in regard to the brilliance and intensity of the color tones.

The problem addressed by the present invention was to provide hair coloring systems based on isatins which would give particularly intensive colors. It has now surprisingly been found that certain N-substituted isatin derivatives are outstanding in satisfying these requirements and are eminently suitable for coloring keratin fibers.

Examples of keratin-containing fibers are wool, furs, skins and human hair. In principle, however, the N-substituted isatin derivatives described in more detail hereinafter may also be used for coloring other natural fibers, for example cotton, jute, sisal, linen or silk, modified natural fibers, for example regenerated cellulose, nitrocellulose, alkyl or hydroxyalkylcellulose or acetyl cellulose and synthetic fibers, for example polyamide, polyacrylonitrile, polyurethane and polyester fibers.

DESCRIPTION OF THE INVENTION

The present invention relates to the use of isatin derivatives corresponding to formula I:

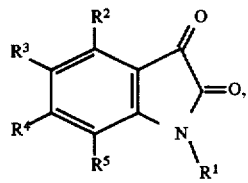

in which $R^1$ is a hydroxy group, an optionally $C_{1-4}$ alkyl- or phenyl-substituted amino group, a $C_{3-8}$ alkenyl, dihydroxy-$(C_{3-6})$-alkyl, trihydroxy-$(C_{4-6})$-alkyl, tetrahydroxy-$(C_{5-6})$-alkyl, pentahydroxy-$C_6$-alkyl, $C_{2-4}$-aminoalkyl, $C_{1-4}$-sulfoalkyl group, an optionally $C_{1-4}$-alkyl-substituted 2-furylmethyl, 2-thienylmethyl, 2-pyridylmethyl, 3-pyridylmethyl, 4-pyridylmethyl group or an aralkyl group corresponding to formula (II):

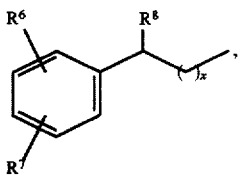

in which $R^6$ and $R^7$ independently of one another represent hydrogens, halogen atoms, hydroxy groups, amino groups optionally substituted by $C_{1-4}$ alkyl or phenyl, $C_{1-4}$ alkyl groups, $C_{1-4}$ alkoxy groups, carboxy groups or sulfo groups and $R^8$ is hydrogen, a $C_{1-4}$ alkyl group or a $C_{2-4}$ hydroxyalkyl group and x=0, 1 or 2, and $R^2$, $R^3$, $R^4$ and $R^5$ independently of one another represent hydrogens, hydroxy groups, halogen atoms, nitro groups, sulfo groups, carboxyl groups, $C_{1-4}$ alkyl groups, $C_{1-4}$ alkoxy groups or $NR^9R^{10}$ groups, where $R^9$ and $R^{10}$ independently of one another represent hydrogen, $C_{1-4}$ alkyl groups or $C_{2-4}$ hydroxyalkyl groups, and two adjacent groups $R^3$, $R^4$ and $R^5$ may even represent an alkylenedioxy group containing 1 to 4 carbon atoms, and water-soluble salts thereof for coloring keratin-containing fibers.

Examples of water-soluble salts are inter alia the alkali metal or ammonium salts of acidic isatins corresponding to formula I and the hydrochlorides, hydrobromides or hydrogen sulfates of basic isatins corresponding to formula 1.

The isatins corresponding to formula I are either compounds known from the literature or may be prepared by standard syntheses known from the literature, inter alia by reaction of isatin or isatin derivatives substituted in the benzene nucleus or sodium salts thereof with corresponding halogen or epoxy compounds. Examples of isatins corresponding to formula I are N-(2,3-dihydroxypropyl)-, N-(2-sulfoethyl)-, (3-sulfopropyl)-, N-allyl-, N-(2-dimethylamino)-, N-(2-pyrrolidino)-, N-(2-piperidino)-, (2-morpholinoethyl)-, N-(2-furylmethyl)-, N-(2-thienylmethyl)-, N-(2-, N-(3- or N-(4-pyridylmethyl)-isatin, N-allyl isatin-5-sulfonic acid, 5-chloro-, 5-methyl-N-(hydroxyethyl)-isatin, 5,7-dichloro-, 5-nitro-N-allyl isatin and the alkali metal salts of the acidic compounds.

Isatin derivatives corresponding to formula 1, in which $R^1$ is an allyl group, a hydroxy group or a 2-sulfoethyl or 2-sulfopropyl group and $R^2$ to $R^5$ are hydrogens are preferably used for coloring keratin-containing fibers.

The isatin derivatives corresponding to formula I give yellow color tones. Particularly brilliant colors in the yellow, red and violet and black ranges with good fastness properties (fastness to light, washing and rubbing) are obtained when the isatin derivatives corresponding to formula I are used together with aminofunctional compounds, for example primary aliphatic amines containing at least one additional amino or $C_{1-4}$ alkoxy group in the C chain, aromatic di- and trihydroxy compounds, for example pyrogallol, hydroxyhydroquinone, phloroglucinol, resorcinol, 2-, 4-methyl resorcinol, 3-dimethylaminophenol, or together with heterocyclic aromatic compounds.

Particularly suitable aminofunctional compounds are amino acids and oligopeptides. Accordingly, the present invention also relates to formulations for coloring keratin-containing fibers containing at least one isatin derivative corresponding to formula I and at least one amino acid or an oligopeptide made up of 2 to 9 amino acids.

Suitable amino acids are any naturally occurring and synthetic amino acids, for example the amino acids obtainable by hydrolysis from vegetable or animal proteins, for example collagen, keratin, casein, elastin, soya protein, wheat gluten or almond protein. Both amino acids showing an acidic reaction and those showing an alkaline reaction may be used.

Suitable oligopeptides are any oligopeptides produced from naturally occurring and synthetic amino acids. The oligopeptides may be naturally occurring or synthetic oligopeptides and also the oligopeptides present in polypeptide or protein hydrolyzates providing they are sufficiently soluble in water for use in the coloring formulations according to the invention. Examples are glutathione and the oligopeptides present in the hydrolyzates of collagen, keratin, casein, elastin, soya protein, wheat gluten or almond protein.

However, amino acids or oligopeptides selected from the group consisting of arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine, glutathione are particularly suitable for use in the coloring formulations according to the invention.

The present invention also relates to formulations for coloring keratin-containing fibers containing at least one isatin derivative corresponding to formula I and at least one aromatic amine corresponding to formula III:

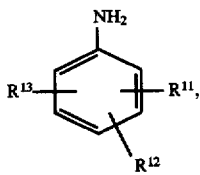

(III)

in which $R^{11}$, $R^{12}$ and $R^{13}$ are hydrogens, $C_{1-4}$ alkyl groups, $C_14$ alkoxy groups, hydroxy groups, $C_{2-4}$ hydroxyalkyl groups, carboxyl groups, sulfo groups, $C_{1-4}$ aminoalkyl groups or $NR^{14}R^{15}$ groups, where $R^{14}$ and $R^{15}$ independently of one another are hydrogens, $C_{1-4}$ alkyl groups, aryl groups or $C_{2-4}$ hydroxyalkyl groups; two of the groups $R^{11}$, $R^{12}$ and $R^{13}$ together may also form a fused benzene ring optionally substituted by $C_{1-4}$ alkyl, hydroxy, carboxyl, sulfo, $C_{1-4}$ aminoalkyl or amino.

Examples are p-phenylenediamine, 3-amino-6-methylphenol, o-phenylenediamine, sulfanilic acid, 1,5-, 1,8-, 2,3-diaminonaphthalene, 6-amino-1-naphthol-3-sulfonic acid, 4-amino-, 4,4'-diaminodiphenylamine, 4,4'-diaminodiphenylamine-2-sulfonic acid, 4-aminodiphenylamine, N,N'-bis-(2-hydroxyethyl)-p-phenylenediamine, 4-dimethylanilinoaniline.

Preferred coloring formulations are those in which the aromatic amine of formula III is selected from the group consisting of p-tolylenediamine, 4-aminophenol, 4-amino-2-aminomethylphenol, 3,4-diaminobenzoic acid, 1-(β-hydroxyethyl)-2,5-diaminobenzene.

The present invention also relates to formulations for coloring keratin-containing fibers containing at least one isatin derivative corresponding to formula I and at least one aromatic amine corresponding to formula IV:

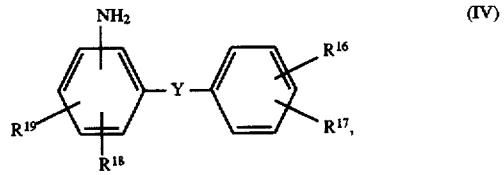

(IV)

in which Y is a direct bond or a group CO, SO, O, S, $NR^{20}$, where $R^{20}$ is hydrogen, $C_{1-4}$ alkyl or $C_{2-4}$ hydroxyalkyl, or $O-(CH_2-Z-CH_2-O)_m$, where Z is a direct bond, a group $CH_2$, CHOH or $CH_2OC_2H_4OCH_2$ and m is an integer of 1 to 4, or Y may even be a saturated or unsaturated alkylene group containing 1 to 4 carbon atoms which may optionally be substituted by OH and $R^{16}$, $R^{17}$, $R^{18}$ and $R^{19}$ are hydrogens, $C_{1-4}$ alkyl groups, $C_{2-4}$ hydroxyalkyl groups, $C_{2-4}$-($C_{1-4}$-alkoxy)-alkyl groups or groups $NR^{21}PR^{22}$ or $OR^{23}$, where $R^{21}$, $R^{22}$ and $R^{23}$ independently of one another represent hydrogens, $C_{1-4}$ alkyl groups, $C_{1-4}$ alkoxy groups, $C_{2-4}$ hydroxyalkyl groups or $C_{2-4}$-($C_{1-4}$-alkoxy)-alkyl groups, with the proviso that at least one of the groups $R^{16}$ and $R^{17}$ and one of the groups $R^{18}$ and $R^{19}$ is a group $NR^{21}R^{22}$ or $OR^{23}$.

Coloring formulations in which the aromatic amine of formula III is 1,3-bis-(2,4-diaminophenoxy)-propane, 1,8-bis-(2,5-diaminophenoxy)-3,6-dioxaoctane or 4,4'-diaminodiphenylamine are preferred.

The present invention also relates to formulations for coloring keratin-containing fibers containing at least one isatin derivative corresponding to formula I and at least one aminopyrimidine corresponding to formula V:

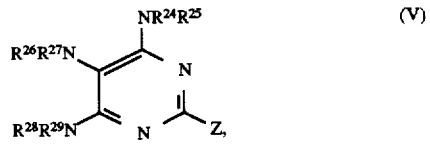

(V)

in which $R^{24}$, $R^{25}$, $R^{26}$, $R^{27}$, $R^{28}$ and $R^{29}$ independently of one another are hydrogens, $C_{1-4}$ alkyl groups or $C_{2-4}$ hydroxyalkyl groups and Z is hydrogen, an OH group or an $NR^{30}R^{31}$ group, where $R^{30}$ and $R^{31}$ independently of one another are hydrogens, $C_{1-4}$ alkyl groups or $C_{2-4}$ hydroxyalkyl groups.

Preferred coloring formulations are those in which unsubstituted 2,4,5,6-tetraaminopyrimidine is used.

Other substances which may be used together with isatin derivatives corresponding to formula I are heterocycles, for example pyrrole, 2,5-dimethyl-3-ethyl pyrrole, 2-, 3-, 4-amino-, 2-amino-3-hydroxy-, 2,6-diamino-, 2,5-diamino-, 2,3-diamino-, 2-dimethylamino-5-amino-, 3-amino-2-methylamino-6-methoxy-, 2,3-diamino-6-methoxy-, 2,4,5-triamino-, 2,6-dihydroxy-3,4-dimethyl pyridine, 4,5,6-triamino-, 4-hydroxy-2,5,6-triamino-, 2,4,5,6-tetraamino-, 2-methylamino-4,5,6-triamino-, 2,4-, 4,5-diamino-, 2-amino-4-methoxy-6-methyl pyrimidine, 3,5-diaminopyrazole, -1,2,4-triazole, 3-amino-, 3-amino-5-hydroxypyrazole, 2-, 3-, 8-aminoquinoline, 4-aminoquinaldine, 2-, 6-aminonicotinic acid, 5-aminoisoquinoline, 4-, 5-, 6-, 7-aminoindole, 5-, 6-aminoindazole, 5-, 7-aminobenzimidazole, -benzothiazole. Indole and indoline derivatives are particularly suitable.

The present invention also relates to formulations for coloring keratin-containing fibers containing at least one isatin derivative corresponding to formula I and
at least one indole derivative corresponding to formula VIa:

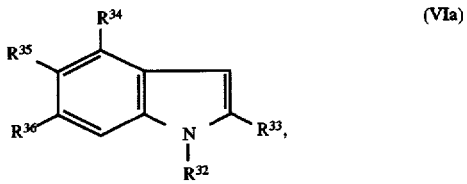

in which $R^{32}$ is hydrogen, a $C_{1-4}$ alkyl or $C_{2-4}$ acyl group, $R^{33}$ is hydrogen or a carboxyl group and $R^{34}$, $R^{35}$ and $R^{36}$ are hydrogens, $C_{1-4}$ alkyl groups, $C_{2-4}$ acyloxy groups, hydroxy groups, amino groups or $C_{1-4}$ alkoxy groups, or
at least one indoline derivative corresponding to formula VIb:

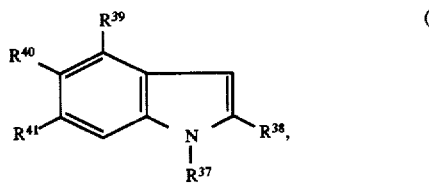

in which $R^{37}$ is hydrogen, a $C_{1-4}$ alkyl or $C_{2-4}$ acyl group, $R^{38}$ is hydrogen or a carboxyl group and $R^{39}$, $R^{40}$ and $R^{41}$ are hydrogens, $C_{1-4}$ alkyl groups, $C_{2-4}$ acyloxy groups, hydroxy groups, amino groups or $C_{1-4}$ alkoxy groups.

Preferred coloring formulations are those in which the indole derivative corresponding to formula VIa or the indoline derivative corresponding to formula VIb is selected from the group consisting of 5,6-dihydroxyindole, 5,6-diacetoxyindole, 4-hydroxyindoline, 6-aminoindoline and 5,6-dihydroxyindoline.

Several different isatin derivatives corresponding to formula I may also be used together in the coloring formulations according to the invention. Several different amino acids or oligopeptides and several different compounds corresponding to formulae II, IV, V, VIa and VIb may also be used together.

The coloring formulations according to the invention give intensive colors at physiologically tolerable temperatures of below 45° C. Accordingly, they are particularly suitable for coloring human hair.

For application to human hair, the coloring formulations according to the invention may be incorporated in a water-containing cosmetic carrier. Suitable water-containing cosmetic carriers are, for example, creams, emulsions, gels or even surfactant-containing foaming solutions, such as shampoos for example, or other preparations which are suitable for application to the hair. The isatins corresponding to formula I and also the amino acids and oligopeptides or the compounds corresponding to formulae III, IV, V, VIa and VIb are each present in quantities of 0.01 to 20% by weight and preferably 1 to 7% by weight, based on the coloring preparation as a whole.

The water-containing cosmetic carrier typically contains wetting agents and emulsifiers, such as anionic, nonionic or ampholytic surfactants, for example fatty alcohol sulfates, alkane sulfonates, α-olefin sulfonates, fatty alcohol polyglycol ether sulfates, alkyl glycosides, ethylene oxide adducts with fatty alcohols, with fatty acids, with alkylphenols, with sorbitan fatty acid esters, with fatty acid partial glycerides and fatty acid alkanolamides; thickeners, for example fatty alcohols, fatty acids, paraffin oils, fatty acid esters and other fatty components in emulsified form; water-soluble polymeric thickeners, such as natural gums, for example gum arabic, karaya gum, guar gum, carob bean flour, linseed gums and pectin, biosynthetic gums, for example xanthan gum and dextrans, synthetic gums, for example agar agar and algin, starch fractions and derivatives, such as amylose, amylopectin and dextrins, modified cellulose molecules, for example methyl cellulose, hydroxyalkyl cellulose and carboxymethyl cellulose, clays, for example bentonite, or fully synthetic hydrocolloids, for example polyvinyl alcohol or polyvinyl pyrrolidone, hair-care additives, for example water-soluble cationic polymers, anionic polymers, nonionic polymers, amphoteric or zwitterionic polymers, pantothenic acid, vitamins, plant extracts or cholesterol, pH regulators, complexing agents and perfume oils and also reducing agents for stabilizing the ingredients, for example ascorbic acid. Finally, dyes may also be present to color the cosmetic preparations.

The pH value of the ready-to-use coloring preparations is between 2 and 11 and preferably between 5 and 9. Where components oxidizable in air, for example 5,6-dihydroxyindole, 5,6-dihydroxyindoline and derivatives thereof, are used, a mildly alkaline pH value of 7 to 11 and preferably 8 to 10 is of advantage.

To color hair, the coloring formulations according to the invention are applied to the hair in the form of the water-containing cosmetic carrier in a quantity of 100 g, left thereon for around 30 minutes and then rinsed out or washed out with a commercial shampoo.

If the coloring formulations according to the invention are used in the form of a water-containing cosmetic preparation, it is of advantage (but not always necessary) to package the isatin derivative corresponding to formula I separately from the second reactive component, i.e. the amino acid or the oligopeptide or the compounds corresponding to formulae III, IV, V, VIa and VIb.

The two components (isatin derivative of formula I and the second reactive component) may then be applied to the hair either at the same time or even successively. It does not matter which of the two components is applied first. Application of the first component and application of the second component may be separated by a time interval of up to 30 minutes.

However, it is of particular advantage to package all the components together in a water-free powder-form preparation.

Accordingly, the present invention also relates to hair coloring formulations in the form of a powder containing at least one isatin derivative corresponding to formula I in a quantity of 1 to 90% by weight and preferably 20 to 50% by weight and an amino acid or an oligopeptide made up of 2 to 9 amino acids in a quantity of 1 to 90% by weight and preferably 20 to 50% by weight, based on the powder-form coloring formulation as a whole.

Particularly preferred hair coloring formulations are those in which the isatin derivative corresponding to formula I is selected from N-allyl isatin, N-hydroxy isatin and N-(2-sulfoethyl)-isatin and the amino acid or the oligopeptide is selected from arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine and glutathione.

The present invention also relates to hair coloring formulations in the form of a powder containing at least one isatin derivative corresponding to formula I in a quantity of 1 to 90% by weight and preferably 20 to 50% by weight and at least one aromatic amine corresponding to formula III in a quantity of 1 to 90% by weight and preferably 20 to 50% by weight, based on the powder-form coloring formulation as a whole.

Particularly preferred hair coloring formulations are those in which the isatin derivative corresponding to formula I is selected from N-allyl isatin, N-hydroxyisatin, N-(2-sulfoethyl)-isatin and N-(2-sulfopropyl)-isatin and the hydroxyisatin, N-(2-sulfoethyl)-isatin and N-(2-sulfopropyl)-isatin and the aromatic amine corresponding to formula III is selected from the group consisting of p-tolylenediamine, 4-aminophenol, 4-amino-2-aminomethylphenol, 3,4-diaminobenzoic acid, 1-(β-hydroxyethyl)-2,5-diaminobenzene.

The present invention also relates to hair coloring formulations in the form of a powder containing at least one isatin derivative corresponding to formula I in a quantity of 1 to 90% by weight and preferably 20 to 50% by weight and at least one aromatic amine corresponding to formula IV in a quantity of 1 to 90% by weight and preferably 20 to 50% by weight, based on the powder-form coloring formulation as a whole.

Particularly preferred hair coloring formulations are those in which the isatin derivative corresponding to formula I is selected from N-allyl isatin, N-hydroxy isatin, N-(2-sulfoethyl)-isatin and N-(2-sulfopropyl)-isatin and the aromatic amine corresponding to formula IV is 1,3-bis-(2,4-diaminophenoxy)propane.

The present invention also relates to hair coloring formulations in the form of a powder containing at least one isatin derivative corresponding to formula I in a quantity of 1 to 90% by weight and preferably 20 to 50% by weight and at least one aminopyrimidine corresponding to formula V in a quantity of 1 to 90% by weight and preferably 20 to 50% by weight, based on the powder-form coloring formulation as a whole.

Particularly preferred hair coloring formulations are those in which the isatin derivative corresponding to formula I is selected from N-allyl isatin, N-hydroxyisatin, N-(2-sulfoethyl)-isatin and N-(2-sulfopropyl)-isatin and the aminopyrimidine corresponding to formula V is unsubstituted tetraaminopyrimidine.

The present invention also relates to hair coloring formulations in the form of a powder containing at least one isatin derivative corresponding to formula I in a quantity of 1 to 90% by weight and preferably 20 to 50% by weight and at least one indole derivative corresponding to formula VIa or an indoline derivative corresponding to formula VIb in a quantity of 1 to 90% by weight and preferably 20 to 50% by weight, based on the powder-form coloring formulation as a whole.

Particularly preferred hair coloring formulations are those in which the isatin derivative corresponding to formula I is selected from N-allyl isatin, N-hydroxy isatin, N-(2-sulfoethyl)-isatin and N-(2-sulfopropyl)-isatin and the indole derivative corresponding to formula Via and the indoline derivative corresponding to formula VIb are selected from 5,6-dihydroxyindole, 5,6-diacetoxyindole, 4-hydroxyindoline, 6-aminoindoline and 5,6-dihydroxyindoline.

The isatins corresponding to formula I may also advantageously be combined with pyridines such as, for example, 2,6-dihydroxy-3,4-dimethylpyridine, 2-amino-3-hydroxypyridine, $^2$-methylamino-3-amino-6-methoxypyridine, 3,5-diamino-2,6-dimethoxypyridine as a second component.

In the most simple case, the powder-form hair coloring formulations contain only a water-soluble polymeric thickener besides the two reactive components (isatin derivative corresponding to formula I and amino acid or oligopeptide or compounds corresponding to formulae III, IV, V, VIa and VIb). The function of the thickener is to provide the ready-to-use hair coloring preparation obtained after the addition of water with the consistency required for application. Suitable thickeners are, for example, natural gums, for example guar flour, gum arabic, karaya gum, carob bean flour, linseed gums and pectin, biosynthetic gums, such as for example xanthan gum and dextrans, synthetic gums, for example agar agar and algin, starch fractions and derivatives, such as amylose, amylopectin and dextrins, modified cellulose molecules, for example methyl cellulose, hydroxyalkyl cellulose and carboxymethyl cellulose.

Other optional components in the powder-form hair coloring formulations are metal salts, for example the acetates, sulfates, chlorides, bromides, carbonates, glycolates, lactates or gluconates of the alkali and alkaline earth metals and of zinc and manganese(I I), surfactants, for example anionic, nonionic, amphoteric or zwitterionic or cationic surfactants, hair-care additives, for example water-soluble cationic polymers, anionic polymers, amphoteric or zwitterionic polymers, pantothenic acid, vitamins, plant extracts, complexing agents, perfume components and also reducing agents, for example ascorbic acid.

To prepare the ready-to-use hair coloring preparation, 1 to 30 g and preferably 3 to 15 g of the powder are made up to 100 g with hot water (90° to 100° C.). Water/alcohol mixtures or other cosmetically compatible solvents may also be used to dissolve the powder. Individual components of the mixture may even be separately dry-blended and stored.

After cooling to around 40° C., the ready-to-use hair coloring preparation is applied to the hair and left thereon for 30 minutes. The hair is then rinsed or washed with a commercial hair shampoo.

In one particular method of coloring, the components are heated to boiling point in water and allowed to react with one another, the reaction mixture is cooled and the deposit is filtered off and then dispersed in water for use as a substantive dye for coloring hair.

The following Examples are intended to illustrate the invention without limiting it in any way.

EXAMPLES

A suspension of 10 mmoles of an isatin corresponding to formula I and 10 mmoles of a second component in 100 ml of water was prepared. The suspension was heated to boiling temperature and filtered after cooling. The pH value was then adjusted to 6. Strands of 90% grey, but non-pretreated human hair were then placed in this coloring solution for 30 minutes at 30° C. The particular coloring temperatures, coloring times, color tones and depths of color are shown in Tables 1 to 3.

Depth of color was evaluated on the following scale:

−: Very pale color, if any
(+): Weak intensity
+: Medium intensity
+(+): Medium to strong intensity
++Strong intensity
++(+): Strong to very strong intensity
+++: Very strong intensity

TABLE 1

Coloring with N-allyl isatin

| Second component | Color tone | Depth of color |
|---|---|---|
| — | Pale yellow | (+) |
| 2,5-Diaminotoluene $H_2SO_4$ | Red-brown | ++(+) |
| 2,4,5,6-Tetraaminopyrimidine $H_2SO_4$ | Dark orange | ++(+) |
| 3,4-Diaminobenzoic acid | Light brown-orange | + |
| 2-(2,5-Diaminophenyl)-ethanol $H_2SO_4$ | Brown-red | ++(+) |
| 1,8-Bis-(2,5-diaminophenoxy)-3,6-dioxaoctane 4HCl | Dark grey | ++(+) |
| 2-Aminomethyl-3-amino-6-methoxy-pyrimidine 2HCl | Dark yellow-grey | ++(+) |
| 2-Aminomethyl-4-aminophenol 2HCl | Orange | ++ |
| 1,3-Bis-(2,4-diaminophenoxy)-propane 4HCl | Beige-grey | + |
| 4-(4-Amino-n-toluidino)-phenol | Light grey-violet | (+) |
| N,N-Dimethyl-p-phenylenediamine $H_2SO_4$ | Dark violet | +++ |
| N-Phenyl-p-phenylenediamine HCl | Light brown | +(+) |
| 4,4'-Diaminodephenylamine $H_2SO_4$ | Dark violet-blue | +++ |
| N-(4-Methoxyphenyl)-p-phenylene-diamine HCl | Light brown | +(+) |
| 4,4'-Diaminodiphenylamine-2-sulfonic acid | Violet red | +++ |
| 2,4-Dimethyl-3-ethyl pyrrole | Yellow | + |
| 1-(o-Aminophenyl)-pyrrole | Yellow | +(+) |
| N-methyl pyrrole | Yellow | +(+) |
| L-Histidine | Olive yellow | + |
| L-Arginine | Pink | + |
| L-Tryptophan | Pale yellow | (+) |
| Pyrrole | Olive yellow | (+) |
| L-Ornithine HCl | Pale yellow | (+) |
| 2,6-Dimethoxy-3,5-diaminopyridine HCl | Green-black | +++ |

TABLE 2

Coloring with N-hydroxyisatin

| Second component | Color tone | Depth of color |
|---|---|---|
| — | Pale yellow | (+) |
| p-Tolylenediamine $H_2SO_4$ | Copper | ++ |
| Tetraaminopyrimidine $H_2SO_4$ | Orange-copper | ++ |
| 2-(2,5-Diaminophenyl)-ethanol $H_2SO_4$ | Copper | ++ |
| 1,8-Bis-(2,5-diaminophenoxy-3,6-dioxa-octane 4HCl | Violet-brown | ++ |

TABLE 3

Coloring with N-(2-sulfoethyl)-isatin

| Second component | Color tone | Depth of color |
|---|---|---|
| — | Yellow | + |
| 2,5-Diaminotoluene $H_2SO_4$ | Violet-red | ++(+) |
| 2,4,5,6-Tetraaminopyrimidine $H_2SO_4$ | Dark copper | ++ |
| 3,4-Diaminobenzoic acid | Yellow-beige | (+) |
| 2-(2,5-Diaminophenyl)-ethanol $H_2SO_4$ | Copper | ++ |
| 1,8-Bis-(2,5-diaminophenoxy)-3,6-dioxa-octane 4HCl | Dark grey | ++ |
| 2-Methylamino-3-amino-6-methoxy-pyridine 2HCl | Pale violet | (+) |
| 2-Aminomethyl-4-aminophenol 2HCl | Deep yellow | ++ |
| 1,3-Bis-(2,4-diaminophenoxy)-propane 4HCl | Olive-grey | + |
| N,N-Dimethyl-p-phenylenediamine $H_2SO_4$ | Red-violet | ++(+) |
| 4,4-Diaminodiphenylamine $H_2SO_4$ | Dark blue-grey | ++(+) |
| 4,4-Diaminodiphenylamine-2-sulfonic acid | Light violet-red | +(+) |
| 2,4-Dimethyl-3-ethyl pyrrole | Yellow-brown | ++ |
| L-Tryptophan | Brown-yellow | + |
| L-Tyrosine | Yellow | + |

TABLE 3-continued

Coloring with N-(2-sulfoethyl)-isatin

| Second component | Color tone | Depth of color |
|---|---|---|
| Pyrrole | Pale | |
| 2,6-Dimethoxy-3,5-diaminopyridine | Green-black | +++ |

What is claimed is:

1. The process of coloring keratin-containing fibers comprising contacting said fibers with an isatin derivative corresponding to formula (I):

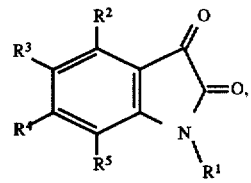

in which $R^1$ is a hydroxy group, an optionally $C_{1-4}$-alkyl- or phenyl-substituted amino group, a $C_{3-8}$ alkenyl, dihydroxy-$(C_{3-6})$-alkyl, trihydroxy-$(C_{4-6})$-alkyl, tetrahydroxy-$(C_{5-6})$-alkyl, pentahydroxy-$C_6$-alkyl, $C_{2-4}$-aminoalkyl, $C_{1-4}$-sulfoalkyl group, an optionally $C_{1-4}$-alkyl-substituted 2-furylmethyl, 2-thienylmethyl, 2-pyridylmethyl, 3-pyridylmethyl, 4-pyridylmethyl group or an aralkyl group corresponding to formula (II):

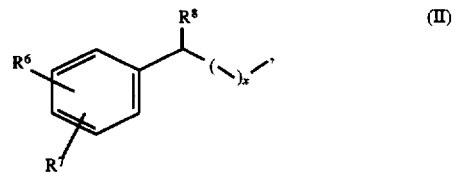

in which $R^6$ and $R^7$ independently of one another represent hydrogen, halogen atoms, hydroxy groups, amino groups optionally substituted by $C_{1-4}$ alkyl or phenyl, $C_{1-4}$ alkyl groups, $C_{1-4}$ alkoxy groups, carboxy groups or sulfo groups and $R^8$ is hydrogen, a $C_{1-4}$ alkyl group or a $C_{2-4}$ hydroxyalkyl group and x=0, 1 or 2, and $R^2$, $R^3$, $R^4$ and $R^5$ independently of one another represent hydrogen, hydroxy groups, halogen atoms, nitro groups, sulfo groups, carboxyl groups, $C_{1-4}$ alkyl groups, $C_{1-4}$ alkoxy groups or $NR^9R^{10}$ groups, wherein $R^9$ and $R^{10}$ independently of one another represent hydrogen, $C_{1-4}$ alkyl groups or $C_{2-4}$ hydroxyalkyl groups, and two adjacent groups $R^3$, $R^4$ and $R^5$ may represent an alkylenedioxy group containing 1 to 4 carbon atoms, and water-soluble salts thereof.

2. A process as in claim 1 wherein $R^1$ is an allyl group, a hydroxy group or a 2-sulfoethyl or 2-sulfopropyl group and $R^2$ to $R^5$ are hydrogen.

3. A process as in claim 1 including contacting said fibers with at least one amino acid or an oligopeptide containing 2 to 9 amino acids.

4. A process as in claim 3, wherein said amino acid or said oligopeptide is selected from the group consisting of arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine and glutathione.

5. A process as in claim 1 including contacting said fibers with at least one aromatic amine corresponding to formula (III):

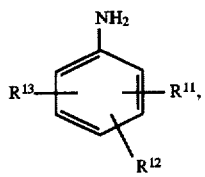

in which $R^{11}$, $R^{12}$ and $R^{13}$ are hydrogen, $C_{1-4}$ alkyl groups, $C_{1-4}$ alkoxy groups, hydroxy groups, $C_{2-4}$ hydroxyalkyl groups, carboxyl groups, sulfo groups, $C_{1-4}$ aminoalkyl groups or $NR^4R^{15}$ groups, wherein $R^{14}$ and $R^{15}$ independently of one another are hydrogen, $C_{1-4}$ alkyl groups, aryl groups or $C_{2-4}$ hydroxyalkyl groups; two of the groups $R^{11}$, $R^{12}$ and $R^{13}$ together may form a fused benzene ring optionally substituted by a $C_{1-4}$ alkyl, hydroxy, carboxyl, sulfo, $C_{1-4}$ aminoalkyl or amino group.

6. A process as in claim 5 wherein said aromatic amine corresponding to formula (III) is selected from the group consisting of p-tolylenediamine, 4-aminophenol, 4-amino-2-aminomethylphenol, 3,4-diaminobenzoic acid, and 1-(β-hydroxyethyl)-2,5-diaminobenzene.

7. A process as in claim 1 including contacting said fibers with at least one aromatic amine corresponding to formula (IV):

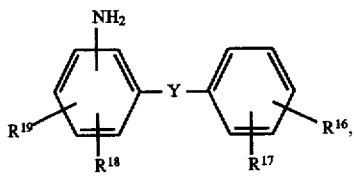

in which Y is a direct bond or a group CO, SO, O, S, $NR^{20}$, wherein $R^{20}$ is hydrogen, $C_{1-4}$ alkyl or $C_{2-4}$ hydroxyalkyl, or $O-(CH_2-Z-CH_2-O)_m$, wherein Z is a direct bond, a group $CH_2$, CHOH or $CH_2OC_2H_4OCH_2$ and m is an integer of 1 to 4, or Y is a saturated or unsaturated alkylene group containing 1 to 4 carbon atoms which is optionally substituted by OH and $R^{16}$, $R^{17}$, $R^{18}$ and $R^{19}$ are hydrogen, C14 alkyl groups, C24 hydroxyalkyl groups, $C_{2-4}$-($C_{1-4}$-alkoxy)-alkyl groups or groups $NR^{21}R^{22}$ or $OR^{23}$, wherein $R^{21}$, $R^{22}$ and $R^{23}$ independently of one another represent hydrogen, $C_{1-4}$ alkyl groups, $C_{2-4}$ $C_{1-4}$ alkoxy groups, $C_{2-4}$ hydroxyalkyl groups or $C_{2-4}$-($C_{1-4}$-alkoxy)-alkyl groups, with the proviso that at least one of the groups $R^{16}$ and $R^{17}$ and one of the groups $R^{18}$ and $R^{19}$ is a group $NR^{21}R_{22}$ or $OR^{23}$.

8. A process as in claim 7 wherein said aromatic amine corresponding to formula (IV) is selected from 1,3-bis-(2,4-diaminophenoxy)-propane, 1,8-bis-(2,5-diaminophenoxy)-3,6-dioxaoctane and 4,4'-diaminodiphenylamine.

9. A process as in claim 1 including contacting said fibers with at least one aminopyrimidine corresponding to formula (V):

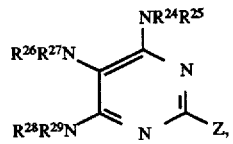

in which $R^{24}$, $R^{25}$, $R^{26}$, $R^{27}$, $R^{28}$ and $R^{29}$ independently of one another are hydrogen, $C_{1-4}$ alkyl groups or $C_{2-4}$ hydroxyalkyl groups and Z is hydrogen, an OH group or an $NR^{30}R^{31}$ group, wherein $R^{30}$ and $R^{31}$ independently of one another are hydrogen, $C_{1-4}$ alkyl groups or $C_{2-4}$ hydroxyalkyl groups.

10. A process as in claim 9 wherein the substituents $R^{24}$ to $R^{29}$ in tetraaminopyrimidine corresponding to formula (V) are hydrogens.

11. A process as in claim 1 including contacting said fibers with at least one indole derivative corresponding to formula (VIa):

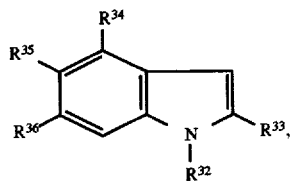

in which $R^{32}$ is hydrogen, a $C_{1-4}$ alkyl or $C_{2-4}$ acyl group, $R^{33}$ is hydrogen or a carboxyl group and $R^{34}$, $R^{35}$ and $R^{36}$ are hydrogen, $C_{1-4}$ alkyl groups, $C_{2-4}$ acyloxy groups, hydroxy groups, amino groups or $C_{1-4}$ alkoxy groups, or at least one indoline derivative corresponding to formula (VIb):

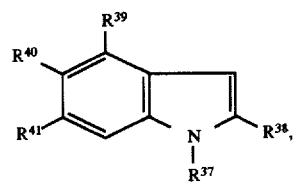

in which $R^{37}$ is hydrogen, a $C_{1-4}$ alkyl or $C_{2-4}$ acyl group, $R^{38}$ is hydrogen or a carboxyl group and $R^{39}$, $R^{40}$ and $R^{41}$ are hydrogen, $C_{1-4}$ alkyl groups, $C_{2-4}$ acyloxy groups, hydroxy groups, amino groups or $C_{1-4}$ alkoxy groups.

12. A process as in claim 11 wherein said indole derivative corresponding to formula (VIa) or said indoline derivative corresponding to formula (VIb) is selected from the group consisting of 5,6-dihydroxyindole, 5,6-diacetoxyindole, 4-hydroxyindoline, 6-aminoindoline and 5,6-dihydroxyindoline.

13. A hair coloring composition comprising an isatin derivative corresponding to formula (I):

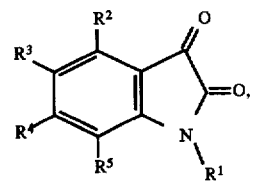

in which $R^1$ is a hydroxy group, an optionally $C_{1-4}$-alkyl- or phenyl-substituted amino group, a $C_{3-8}$ alkenyl, dihydroxy-($C_{3-6}$)-alkyl, trihydroxy-($C_{4-6}$)-alkyl, tetrahydroxy-($C_{5-6}$)-alkyl, pentahydroxy-$C_6$-alkyl, $C_{2-4}$-aminoalkyl, $C_{1-4}$-sulfoalkyl group, an optionally $C_{1-4}$-alkyl-substituted 2-furylmethyl, 2-thienylmethyl, 2-pyridylmethyl, 3-pyridylmethyl, 4-pyridylmethyl group or an aralkyl group corresponding to formula (II):

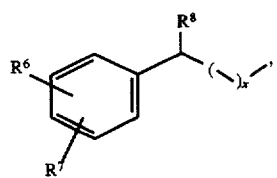

in which $R^6$ and $R^7$ independently of one another represent hydrogen, halogen atoms, hydroxy groups, amino groups optionally substituted by $C_{1-4}$ alkyl or phenyl, $C_{1-4}$ alkyl groups, $C_{1-4}$ alkoxy groups, carboxy groups or sulfo groups and $R^2$ is hydrogen, a $C_{1-4}$ alkyl group or a $C_{2-4}$ hydroxyalkyl group and x=0, 1 or 2, and $R^2$, $R^3$, $R^4$ and $R^5$ independently of one another represent hydrogen, hydroxy groups, halogen atoms, nitro groups, sulfo groups, carboxyl groups, $C_{1-4}$ alkyl groups, $C_{1-4}$ alkoxy groups or $NR^9R^{10}$ groups, wherein $R^9$ and $R^{10}$ independently of one another represent hydrogen, $C_{1-4}$ alkyl groups or $C_{2-4}$ hydroxyalkyl groups, and two adjacent groups $R^3$, $R^4$ and $R^5$ may represent an alkylenedioxy group containing 1 to 4 carbon atoms, and water-soluble salts thereof; and an aminofunctional compound selected from the group consisting of (a) an amino acid or an oligopeptide containing 2 to 9 amino acids, (b) an aromatic amine corresponding to formula (III):

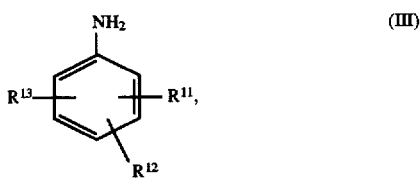

in which $R^{11}$, $R^{12}$, and $R^{13}$ are hydrogen $C_{1-4}$ alkyl groups, $C_{1-4}$ alkoxy groups, hydroxy groups, $C_{2-4}$ hydrogen groups, carboxyl groups, sulfo groups, $C_{1-4}$ aminoalkyl groups or $NR^{14}R^{15}$ groups, wherein $R^{14}$ and $R^{15}$ independently of one another are hydrogen, $C_{1-4}$ alkyl groups, aryl groups or $C_{2-4}$ hydroxyalkyl groups, two of the groups $R^{11}$, $R^{12}$ and $R^{13}$ together may form a fused benzene ring optionally substituted by a $C_{1-4}$ alkyl hydroxy, carboxyl, sulfo, $C_{1-4}$ aminoalkyl or amino group, (c) an aromatic amine corresponding to formula (IV):

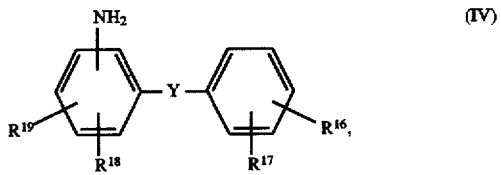

in which Y is a direct bond or a group CO, SO, O, S, $NR^{20}$, wherein $R^{20}$ is hydrogen, $C_{1-4}$ alkyl or 2-4 hydroxyalkyl, or $O-(CH_2-Z-CH_2-O)_m$, wherein Z is a direct bond, a group $CH_2$ or CHOH or $CH_2OC_2H_4OCH_2$ and m is an integer of 1 to 4, or Y is a saturated or unsaturated alkylene group containing 1 to 4 carbon atoms which is optionally substituted by OH and $R^{16}$, $R^{17}$, $R^{18}$ and $R^{19}$ are hydrogen, $C_{1-4}$ alkyl groups, $C_{2-4}$ hydroxyalkyl groups, $C_{2-4}-(C_{1-4}$-alkoxy)-alkyl groups or groups $NR^{21}R^{22}$ or $OR^{23}$, wherein $R^{21}$, $R^{22}$ and $R^{20}$ independently of one another represent hydrogen, $C_{1-4}$ groups, $C_{1-4}$ alkoxy groups, $C_{2-4}$ hydroxyalkyl groups or $C_{2-4}$-alkoxy)-alkyl groups, with the proviso that at least one of the groups $R^{16}$ and $R^{17}$ and one of the groups $R^{18}$ and $R^{19}$ is a group $NR^{21}R^{22}$ or $OR^{23}$, (d) an aminopyrimidine corresponding to formula (V):

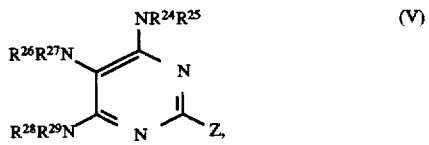

in which $R^{24}$, $R^{25}$, $R^{26}$, $R^{27}$, $R^{28}$ and $R^{29}$ independently of one another are hydrogen, $C_{1-4}$ alkyl groups or $C_{2-4}$ hydroxyalkyl groups and Z is hydrogen, an OH group or an $NR^{30}R^{31}$ group, wherein $R^{30}$ and $R^{31}$ independently of one another are hydrogen, $C_{1-4}$ alkyl groups or $C_{2-4}$ hydroxyalkyl groups, (e) an indole derivative corresponding to formula (VIa):

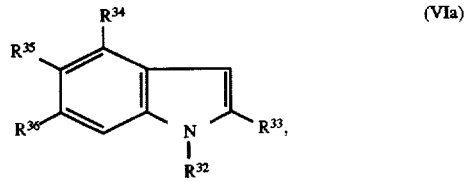

in which $R^{32}$ is hydrogen, a $C_{1-4}$ alkyl or $C_{2-4}$ acyl group, $R^{33}$ is hydrogen or a carboxyl group and $R^{34}$, $R^{35}$ and $R^{36}$ are hydrogen, $C_{1-4}$ alkyl groups, $C_{2-4}$ acyloxy groups, hydroxy groups, amino groups or $C_{1-4}$ alkoxy groups, and (f) an indoline derivative corresponding to formula (VIb):

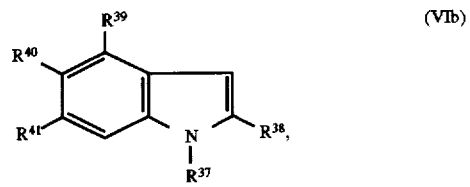

in which $R^{37}$ is hydrogen, a $C_{1-4}$ alkyl or $C_{2-4}$ acyl group, $R^{38}$ is hydrogen or a carboxyl group and $R^{39}$, $R^{40}$ and $R^{41}$ are hydrogen, $C_{1-4}$ alkyl groups, $C_{2-4}$ acyloxy groups, hydroxy groups, amino groups or $C_{1-4}$ alkoxy groups.

14. A composition as in claim 13 wherein $R^1$ is an allyl group, a hydroxy group or a 2-sulfoethyl or 2-sulfopropyl group and $R^2$ to $R^5$ are hydrogen.

15. A composition as in claim 13 containing at least one amino acid or an oligopeptide containing 2 to 9 amino acids.

16. A composition as in claim 13, wherein said amino acid or said oligopeptide is selected from the group consisting of arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine and glutathione.

17. A composition as in claim 13 containing at least one aromatic amine corresponding to formula (III):

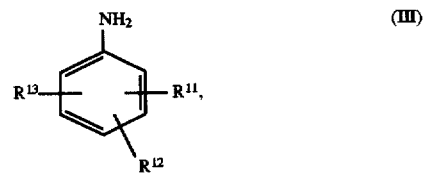

in which $R^{11}$, $R^{12}$ and $R^{13}$ are hydrogen, $C_{1-4}$ alkyl groups, $C_{1-4}$ alkoxy groups, hydroxy groups, $C_{2-4}$ hydroxyalkyl groups, carboxyl groups, sulfo groups, $C_{1-4}$ aminoalkyl groups or $NR^{14}R^{15}$ groups, wherein $R^{14}$ and $R^{15}$ independently of one another are hydrogen, $C_{1-4}$ alkyl groups, aryl groups or $C_{2-4}$ hydroxyalkyl groups; two of the groups $R^{11}$, $R^{12}$ and $R^{13}$ together may form a fused benzene ring optionally substituted by a $C_{1-4}$, alkyl, hydroxy, carboxyl, sulfo, $C_{1-4}$ aminoalkyl or amino group.

18. A composition as in claim 17 wherein said aromatic amine corresponding to formula (III) is selected from the group consisting of p-tolylenediamine, 4-aminophenol, 4-amino-2-aminomethylphenol, 3,4-diaminobenzoic acid, and 1-(β-hydroxyethyl)-2,5-diaminobenzene.

19. A composition as in claim 13 containing at least one aromatic amine corresponding to formula (IV):

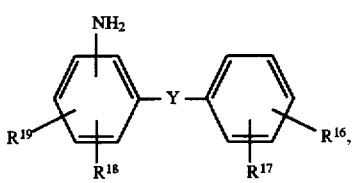

in which Y is a direct bond or a group CO, SO, O, S, $NR^{20}$, wherein $R^{20}$ is hydrogen, $C_{1-4}$ alkyl or $C_{2-4}$ hydroxyalkyl, or $O-(CH_2-Z-CH_2-O)_m$, wherein Z is a direct bond, a group $CH_2$, CHOH or $CH_2OC_2H_4OCH_2$ and m is an integer of 1 to 4, or Y is a saturated or unsaturated alkylene group containing 1 to 4 carbon atoms which is optionally substituted by OH and $R^{16}$, $R^{17}$, $R^{18}$ and $R^{19}$ are hydrogen, $C_{1-4}$ alkyl groups, $C_{2-4}$ hydroxyalkyl groups, $C_{2-4}$-($C_{1-4}$-alkoxy)-alkyl groups or groups $NR^{21}R^{22}$ or $OR^{23}$, wherein $R^{21}$, $R^{22}$ and $R^{23}$ independently of one another represent hydrogen, $C_{1-4}$ alkyl groups, $C_{1-4}$ alkoxy groups, $C_{2-4}$ hydroxyalkyl groups or $C_{2-4}$-($C_{1-4}$-alkoxy)-alkyl groups, with the proviso that at least one of the groups $R^{16}$ and $R^{17}$ and one of the groups $R^{18}$ and $R^{19}$ is a group $NR^{21}R^{22}$ or $OR^{23}$.

20. A composition as in claim 19 wherein said aromatic amine corresponding to formula (IV) is selected from 1,3-bis-(2,4-diaminophenoxy)-propane, 1,8-bis-(2,5-diaminophenoxy)-3,6-dioxaoctane and 4,4'-diaminodiphenylamine.

21. A composition as in claim 13 containing at least one aminopyrimidine corresponding to formula (V):

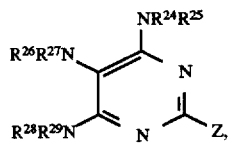

in which $R^{24}$, $R^{25}$, $R^{26}$, $R^{27}$, $R^{28}$ and $R^{29}$ independently of one another are hydrogen, $C_{1-4}$ alkyl groups or $C_{2-4}$ hydroxyalkyl groups and Z is hydrogen, an OH group or an $NR^{30}R^{31}$ group, wherein $R^{30}$ and $R^{31}$ independently of one another are hydrogen, $C_{1-4}$ alkyl groups or $C_{2-4}$ hydroxyalkyl groups.

22. A composition as in claim 21 wherein the substituents $R^{24}$ to $R^{29}$ in formula (V) are hydrogens.

23. A composition as in claim 13 containing at least one indole derivative corresponding to formula (VIa):

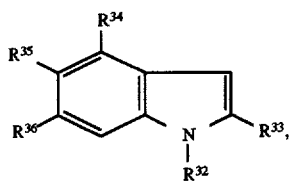

in which $R^{32}$ is hydrogen, a $C_{1-4}$ alkyl or $C_{2-4}$ acyl group, $R^{33}$ is hydrogen or a carboxyl group and $R^{34}$, $R^{35}$ and $R^{36}$ are hydrogen, $C_{1-4}$ alkyl groups, $C_{2-4}$ acyloxy groups, hydroxy groups, amino groups or $C_{1-4}$ alkoxy groups, or at least one indoline derivative corresponding to formula (VIb):

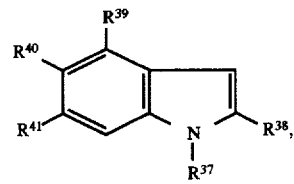

in which $R^{37}$ is hydrogen, a $C_{1-4}$ alkyl or $C_{2-4}$ acyl group, $R^{38}$ is hydrogen or a carboxyl group and $R^{39}$, $R^{40}$ and $R^{41}$ are hydrogen, $C_{1-4}$ alkyl groups, $C_{2-4}$ acyloxy groups, hydroxy groups, amino groups or $C_{1-4}$ alkoxy groups.

24. A composition as in claim 23 wherein said indole derivative corresponding to formula (VIa) or said indoline derivative corresponding to formula (VIb) is selected from the group consisting of 5,6-dihydroxyindole, 5,6-diacetoxyindole, 4-hydroxyindoline, 6-aminoindoline and 5,6-dihydroxyindoline.

25. A composition as in claim 13 in the form of a powder containing at least one isatin derivative corresponding to formula (I) in a quantity of 1% to 90% by weight, and an amino acid or an oligopeptide containing 2 to 9 amino acids in a quantity of 1% to 90% by weight, based on the weight of said composition.

26. A composition as in claim 25 wherein the isatin derivative corresponding to formula (I) is selected from N-allyl isatin, N-hydroxyisatin and N-(2-sulfoethyl)-isatin, and the amino acid or the oligopeptide is selected from arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine and glutathione.

* * * * *